(12) United States Patent
Bogojevic et al.

(10) Patent No.: US 8,548,726 B2
(45) Date of Patent: Oct. 1, 2013

(54) MARKER SYSTEM FOR DETERMINING THE DIAMETER AND AXIAL LOCATION OF A HOLE IN AN INSTRUMENT

(75) Inventors: Aleksander Bogojevic, Münich (DE); Christian Maier, Münich (DE); Georg Christian, Münich (DE); Jörg Uhde, Münich (DE)

(73) Assignee: Brainlab AG, Feldkirchen (DE)

( * ) Notice: Subject to any disclaimer, the term of this patent is extended or adjusted under 35 U.S.C. 154(b) by 1323 days.

(21) Appl. No.: 11/960,102

(22) Filed: Dec. 19, 2007

(65) Prior Publication Data
US 2008/0183387 A1    Jul. 31, 2008

Related U.S. Application Data

(60) Provisional application No. 60/882,772, filed on Dec. 29, 2006.

(30) Foreign Application Priority Data

Dec. 20, 2006 (EP) .................................... 06026421

(51) Int. Cl.
*G06F 17/00* (2006.01)
*G05D 3/00* (2006.01)
*G01B 5/00* (2006.01)

(52) U.S. Cl.
USPC ............................ 701/300; 702/153; 702/157

(58) Field of Classification Search
USPC ......... 701/300, 302, 400, 408; 702/150–153, 702/157; 600/414, 424; 606/130
See application file for complete search history.

(56) References Cited

U.S. PATENT DOCUMENTS

| 6,351,659 | B1 | 2/2002 | Vilsmeier |
| 2004/0054489 | A1 | 3/2004 | Moctezuma De La Barrera et al. |
| 2006/0122491 | A1* | 6/2006 | Murray et al. ................ 600/414 |

FOREIGN PATENT DOCUMENTS

| DE | 196 39 615 | 4/1998 |
| WO | 02/061371 | 8/2002 |
| WO | 2006/029541 | 3/2006 |

* cited by examiner

*Primary Examiner* — Thomas Tarcza
*Assistant Examiner* — Edward Pipala
(74) *Attorney, Agent, or Firm* — Renner, Otto, Boisselle & Sklar, LLP

(57) ABSTRACT

A marker system and method are provided that can determine a shape and an axial location of a rotationally symmetrical hole in an instrument having a plurality of instrument markers.

11 Claims, 4 Drawing Sheets

MARKER SYSTEM FOR DETERMINING THE DIAMETER AND AXIAL LOCATION OF A HOLE IN AN INSTRUMENT

RELATED APPLICATION DATA

This application claims priority of U.S. Provisional Application No. 60/882,772 filed on Dec. 29, 2006, which is incorporated herein by reference in its entirety.

FIELD OF THE INVENTION

The present invention relates generally to medical navigation and, more particularly, to a marker system for determining a diameter and axial location of a bore or hole in an object.

BACKGROUND OF THE INVENTION

Marker means are currently detected by means of a detection means (e.g., a camera or ultrasound detector). The marker means typically comprise three markers arranged in a fixed and predetermined location relative to each other and can be mechanically connected. The markers can be passive or active markers, wherein passive markers reflect signals (e.g., waves and/or radiation) emitted in their direction, and active markers are themselves the source of the signals (e.g., waves and/or radiation). The signals emitted from the (active or passive) markers, which can be wave signals or radiation signals, are detected by the detection means. In order to establish a position of the marker means relative to the detection means, the marker means is preferably moved to provide the detection means with different views of the marker means. On the basis of this, the location of the marker means relative to the detection means then can be determined in a known way, in particular in a spatial reference system. Reference is made in this respect to DE 196 39 615 A1 and the corresponding U.S. Pat. No. 6,351,659, each of which are hereby incorporated by reference in their entirety.

SUMMARY OF THE INVENTION

A marker system is provided that enables a diameter and axial location of a rotationally symmetrical hole or bore in an object (referred to hereinafter as an instrument) to be determined. The term "rotationally symmetrical" as used herein relates to the axis of the hole or bore, i.e., the surface area which surrounds and delineates the hole has a shape which is rotationally symmetrical with respect to the axis in the longitudinal direction (insertion direction into the hole). Examples of rotationally symmetrical holes include cylindrical holes (bores or transit bores), but also can include, for example, conical holes or holes that are configured to be partially spherical (e.g., hemispheres). The term "hole" here includes both transit holes, which penetrate through the instrument, and a recess in the instrument. The marker system can include a body to which markers are attached (referred to as "body markers" below). The body markers can be situated in a predetermined arrangement relative to each other and can exhibit a prior-known size and shape (e.g., a spherical shape). The body thus can comprise a marker means. Preferably, the instrument also comprises a marker means, as will be discussed in more detail below. In general, the following applies to marker means.

The location of the marker means is preferably determined by the position of the marker means in a predetermined reference system. The reference system can be a reference system in which the detection means lies. The location of the marker means can be determined by the positions of the markers, in particular center points of the markers, in the reference system. The positions, for example, can be described using Cartesian coordinates or spherical coordinates. The location of one part (e.g., the detection means or marker means) relative to another part (e.g., the marker means) can be described by spatial angles and/or distances and/or coordinates (in a reference system) and/or vectors and is preferably calculated from the positions describing the location, for example by means of a program running on a computer.

The term "relative location" used here or the expression "location of a part A relative to a part B" thus comprises the concept of the relative positions between the two parts, in particular between the marker means and/or their markers or between a marker means (or its markers) and the detection means. In particular, centers of gravity or center points of the parts can be selected as a punctiform reference point for establishing a position. If the position of one part is known in a reference system, then it is possible, based on the relative location of two parts, to calculate the position of one of the two parts from the position of the other of the two parts.

If the marker means comprises only two markers, a start position is preferably known, and the marker system then allows the location of the marker means to be tracked when the marker means is spatially moved.

The marker means in accordance with the present invention preferably comprises at least two markers, and more preferably three markers. The dimensions of the markers and the location of the markers relative to each other are known and may be available as prior-known data of a data processing means. The shape of the markers is preferably also known.

The marker system preferably also comprises a detection means that detects signals from the at least two markers. As stated above, these signals may be emitted from the markers (either actively emitted by the markers or reflected by the markers). In the latter case, a signal transmitting source, for example an infrared light source, is preferably provided that emits signals (e.g., ultrasound pulses or infrared light) toward the passive markers, wherein the passive markers reflect the signals. A data processing means, such as a computer, allows the location of the marker means relative to the detection means to be calculated, in particular the location of the marker means in a reference system in which the detection means lies, e.g., in a reference system which lies in an operating theater.

If the body has then been provided with a marker means and the instrument to be examined has also been provided with a marker means, then it is possible to determine the relative location of the body relative to the instrument. The location of the axis of the hole relative to the marker means attached to the instrument, and the shape of the hole, are however still unknown.

In order to determine the location of the axis, body markers can be provided on the body as well as rotationally symmetrical extensions. These extensions, for example, can have a cylindrical configuration or a conical configuration (including a truncated cone).

An operator who wishes to measure a characteristic (e.g., a diameter) of a hole in an (arbitrary) instrument uses an instrument that is provided with a marker means. The markers of the marker means are referred to here as "instrument markers", in order to distinguish them from the body markers. The operator searches out the extension that has a diameter that is substantially the same as the diameter of the hole and rotates the instrument around this hole while the signals emitted by the instrument markers are detected by the detection means.

As used herein, substantially the same diameter refers to diameters that are nearly identical (e.g., an exact fit that permits movement of the hole relative to the extension, with little to no interference). Due to the embodiment of the marker system in accordance with the invention, this approach allows both the shape of the hole (e.g., the diameter of a cylindrical hole) and the location of the axis of the hole to be determined.

The detection means in accordance with the invention is embodied to detect signals emitted both by the body markers and by the instrument markers. This allows the data processing means to determine the location of the body markers relative to the instrument markers. In order to make this and/or other determinations, the detection means preferably converts the detected signals into data signals and outputs them to the data processing means.

The data processing means is preferably designed to perform the functions (described in more detail below) of receiving, storing, calculating and determining. The data processing means receives the data signals output by the detection means. In other words, the data processing means receives data signals that represent the location of the body markers relative to the detection means, and data signals that represent the location of the instrument markers relative to the detection means. As already stated above, the instrument is preferably rotated by an operator around an extension that has been fit into the hole in the instrument. A number of locations of the instrument markers relative to the detection means thus arise during this rotational movement. Preferably, at least three locations of the instrument markers relative to the detection means are provided in accordance with the invention. The data processing means can be designed to receive and further process at least three different locations of the instrument markers relative to the detection means. When further processing the different relative locations of the instrument markers (relative to the detection means), it is then preferably assumed that these relative locations lie on a circular trajectory.

An approximating method (fitting method such as for example a least-square fit) is preferably performed to calculate a circular trajectory from the three relative locations, on which the three relative locations at least approximately lie. The data processing means thus has the function of calculating a circular trajectory and the assumption that the at least three different relative locations lie on a circular trajectory. In order to mathematically describe a circular trajectory, the location of the center point and the radius of the circular trajectory, and in particular trigonometric functions (e.g., sine, cosine), are preferably used. Calculating the circular trajectory thus also calculates the location of the center point of the circular trajectory and determines the center point relative to the detection means. Since the location of the center point of the circular trajectory matches the location of the axis of the hole in the instrument, the location of the axis of the hole relative to the detection means is thus also determined.

However, the aforementioned method step of fitting an extension into an instrument hole and then rotating the instrument around said extension not only allows the relative location of the axis of the hole to be determined, but also allows the shape of the hole to be determined. The shape of the hole is preferably described by one or more characteristics. In the case of a cylindrical hole and thus a cylindrical extension, this at least one characteristic, for example, can be the diameter or radius of the hole, and additionally the height of the cylindrical extension. It is, however, also possible to provide rotationally symmetrical extensions of different shapes on the body, e.g., cylindrically shaped, conically shaped or spherically shaped extensions. In this case, the at least one characteristic preferably also includes a characteristic that indicates the configuration, e.g., cylindrical, conical or spherical. If, for example, there are only conically configured extensions comprising a conical tip (i.e., not truncated cones), then the at least one characteristic preferably includes the aperture angle of the cone. In the case of a truncated cone, the height of the truncated cone and/or the radii or diameters of the faces enclosing the truncated cone, for example, may be other characteristics.

In accordance with the invention, the data processing means is designed to determine the at least one characteristic. To this end, the relative locations between the body markers and the axes of the rotationally symmetrical extensions are preferably known and stored in the data processing means. The aforesaid characteristics also can be stored in association with the aforesaid relative locations of the axes relative to the body markers. In particular, at least one characteristic is stored in association with each individual axis.

It is thus possible to calculate, from the data signals, which of the axes match the calculated center point. It is in particular possible to calculate the relative location of the center point and, therefore, of the axis relative to the detection means. From the detected location of the body markers and the stored data concerning the location of the body markers relative to the axes, it is then possible to determine which of the axes matches the center point.

Detecting the instrument markers thus allows the location of the center point of the circular trajectory relative to the detection means to be determined. Detecting the body markers allows the location of the axes relative to the detection means to be determined. Thus, it is possible to determine which of the respective determined locations of the axes relative to the detection means matches the determined location of the center point relative to the detection means. Further, it is possible to determine which axis matches the center point, so as to identify the axis.

If the axis has then been identified, it is then possible to determine, from the stored association between the axis and the characteristics, the characteristic that is associated with the identified axis. The aforesaid method step thus enables both the location of the axis relative to the detection means and therefore also relative to the instrument markers to be determined. In addition, it is simultaneously possible to determine the characteristic of the hole in the instrument. The instrument is thus registered and can be used in any way. The determined location of the axis of the hole relative to the instrument markers, and the at least one characteristic which characterizes the shape of the hole can be stored for a later application of the instrument.

As already stated above, the arrangement of the body markers relative to each other may be known and preferably stored. This arrangement differs from the arrangement (and as applicable the shape) of the instrument markers, which also may be stored. The markers are preferably all spherical. Due to the characteristic arrangement of the body markers and the characteristic arrangement of the instrument markers, it is possible to distinguish the body markers from the instrument markers. When processing the data signals, the data processing means can thus recognize which data signals are to be associated with the body markers and which are to be associated with the instrument markers.

The distance between two extensions is preferably larger than the diameter of one of the extensions, in particular larger than the maximum diameter of the extensions. A preferred range is around 100 to 300% of the diameter of the extension.

The surface from which the extensions protrude is preferably convexly curved or planar. This enables the instrument to be placed directly onto the surface and simultaneously to not obstruct the instrument from being rotated around the extension when the extension has been inserted into the hole in the instrument. A planar embodiment of the surface is preferred, since it is possible to laterally guide the instrument during the rotational movement around the axis of the extension. The intersection points between the axis of the extensions and the aforesaid surface preferably represent points that lie on a trajectory. The trajectory, for example, can be a straight line or a curved line, in particular a closed line (for example a circle or ellipse). This arrangement means that rotating the instrument around one of the axes of the extensions is not obstructed by other extensions.

Alternatively or additionally, the extensions also can be arranged one above the other, such that the axes of the extensions transition into each other, wherein the diameter of the extensions decreases as the distance from the aforesaid surface increases. The diameter preferably decreases in steps (see FIG. 4).

The body on which the extensions are provided also can be designed in a number of parts. One part of the body, which is referred to here as the "extension body" and on which the extensions are provided, can in particular be separate from another part of the body which is referred to here as the "marker unit". A marker means can be provided on the marker unit. In this way, differently configured marker means can be connected to the extension body, so as to be able to use a marker means, which is suitable for the respective application purpose, as the body marker. On the other hand, a number of different extension bodies can of course be connected to a particular marker means. It is then for example possible to select, depending on the shaping of the hole, an extension body comprising cylindrical extensions or one comprising conical extensions, or to select extension bodies having different diameters or characteristics. The connection between the two parts is preferably releasable and, when the parts are connected, spatially fixed, i.e., a relative movement between the marker unit and the extension body is prevented.

BRIEF DESCRIPTION OF THE DRAWINGS

The forgoing and other features of the invention are hereinafter discussed with reference to the drawings.

DETAILED DESCRIPTION

Figure 1:
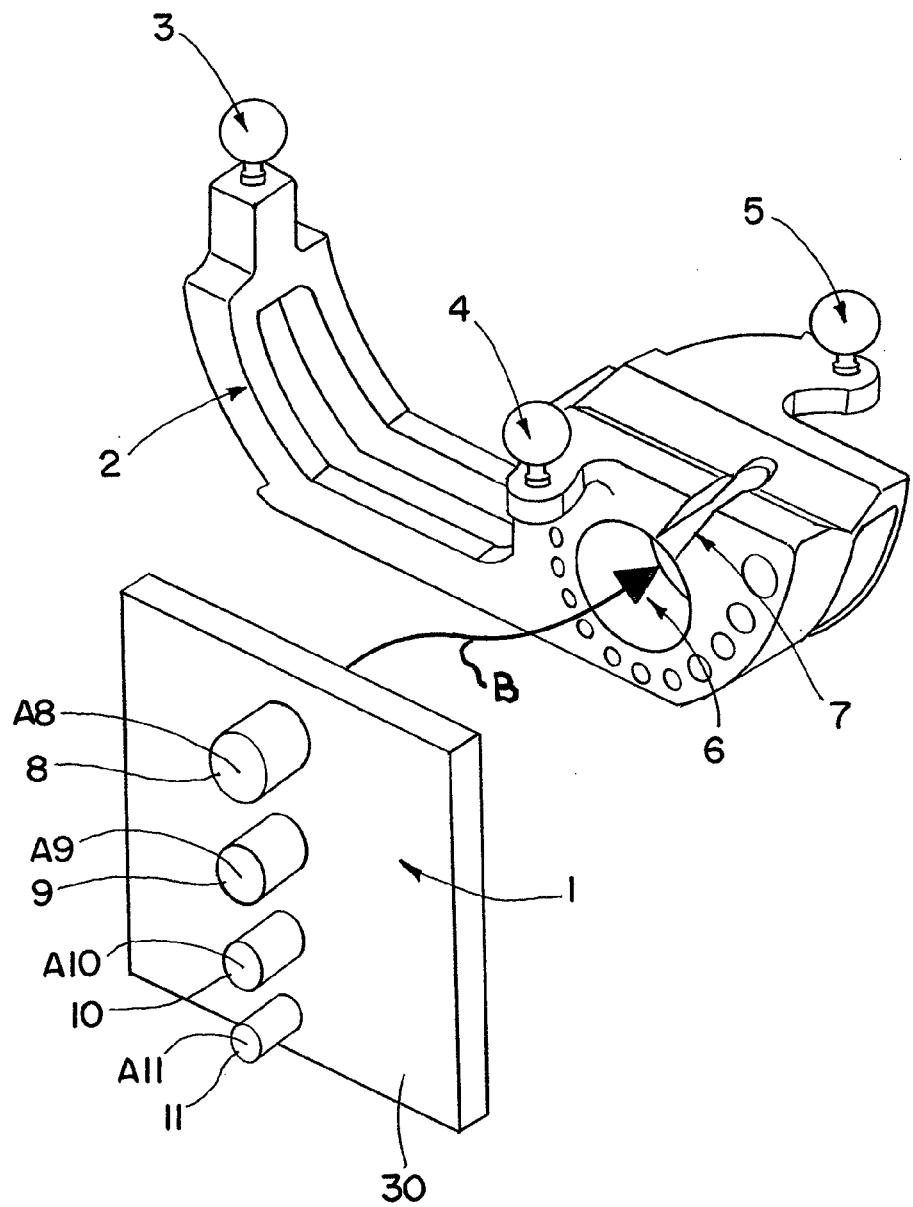
FIG. 1 illustrates an exemplary extension body with markers coupled thereto.

The exemplary extension body 1 shown in FIG. 1 comprises a number of extensions 8, 9, 10 and 11. The extension 8 has an axis A8, the extension 9 has an axis A9, the extension 10 has an axis A10 and the extension 11 has an axis A11. As shown in FIG. 1, the extensions preferably protrude from a level plane 30 of the extension body 1. In the exemplary extension body of FIG. 1, the extensions are designed cylindrically, i.e., they have a constant diameter along their axes. The diameters of the respective extensions preferably differ, and the extensions are preferably arranged in a row. Further, the distance between each extension is preferably at least as large as the diameter of the adjacent extension, and more preferably larger than the diameter of the extension with the largest diameter. The extensions preferably protrude from the plane 30 by the same distance.

The marker unit 2 comprises three markers 3, 4, and 5 having a preferably spherical configuration, wherein a diameter of each marker is the same. The location of the markers 3, 4 and 5 relative to each other is preferably known and in particular characteristic of the marker unit 2. It is thus possible to recognize, from the characteristic arrangement of the markers 3, 4 and 5, the marker unit 2.

In the embodiment shown in FIG. 1, the marker unit 2 is designed as a calibrating device, wherein for calibrating purposes, instruments can be placed on planes of the marker unit 2 or inserted into openings to perform a calibration. This secondary function of the marker unit 2, however, is not further discussed herein.

Figure 2C:
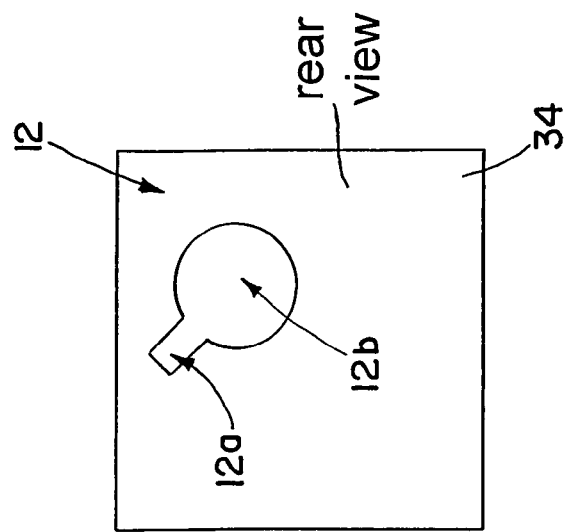
FIG. 2c is a rear view of the extension body of FIG. 1.
Figure 2B:
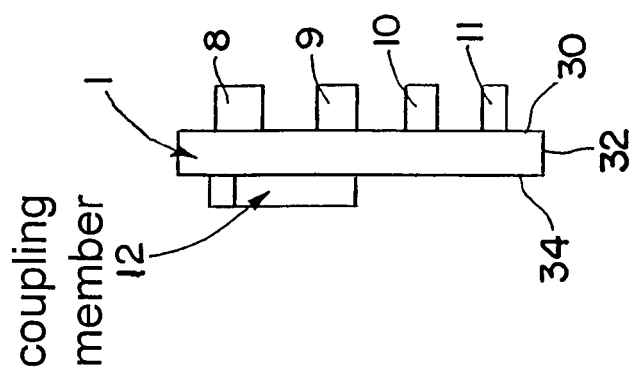
FIG. 2b is a lateral view of the extension body of FIG. 1.
Figure 2A:
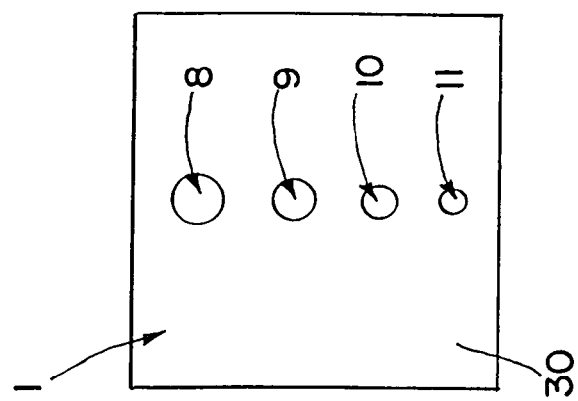
FIG. 2a is a front view of the extension body of FIG. 1.

FIG. 2a shows a front view of the extension body 1, wherein the extensions 8, 9, 10 and 11 are shown in a top view as circles of different diameters. FIG. 2b shows a lateral view of the extension body 1, wherein to the right of the plate 32 that includes the front plane 30, the extensions 8, 9, 10 and 11 are arranged in a row from top to bottom. A coupling member 12 is situated on the rear side 34 of the plate 32 and protrudes from the planar rear side 34. The coupling member 12 is shown in more detail in FIG. 2c. FIG. 2c is a rear view of the extension body 1, in which the coupling member 12 is shown in a top view. It consists of a circular portion 12b and an extension 12a which protrudes from the circular member 12b and blocks rotation.

As shown in FIG. 1, the circular portion 12b is inserted into the circular opening 6 of the marker unit 2, as indicated by the arrow B. In addition, the extension 12a is inserted into the complementarily designed recess 7 of the marker unit 2. The extension 12a, in cooperation with the recess 7, thus prevents the extension body 1 from rotating relative to the marker unit 2. The coupling member 12 is preferably configured in an exact fit to ensure a stable relative location between the extension body 1 and the marker unit 2. Additionally or alternatively, a catch-like coupling can also be provided.

Figure 3:
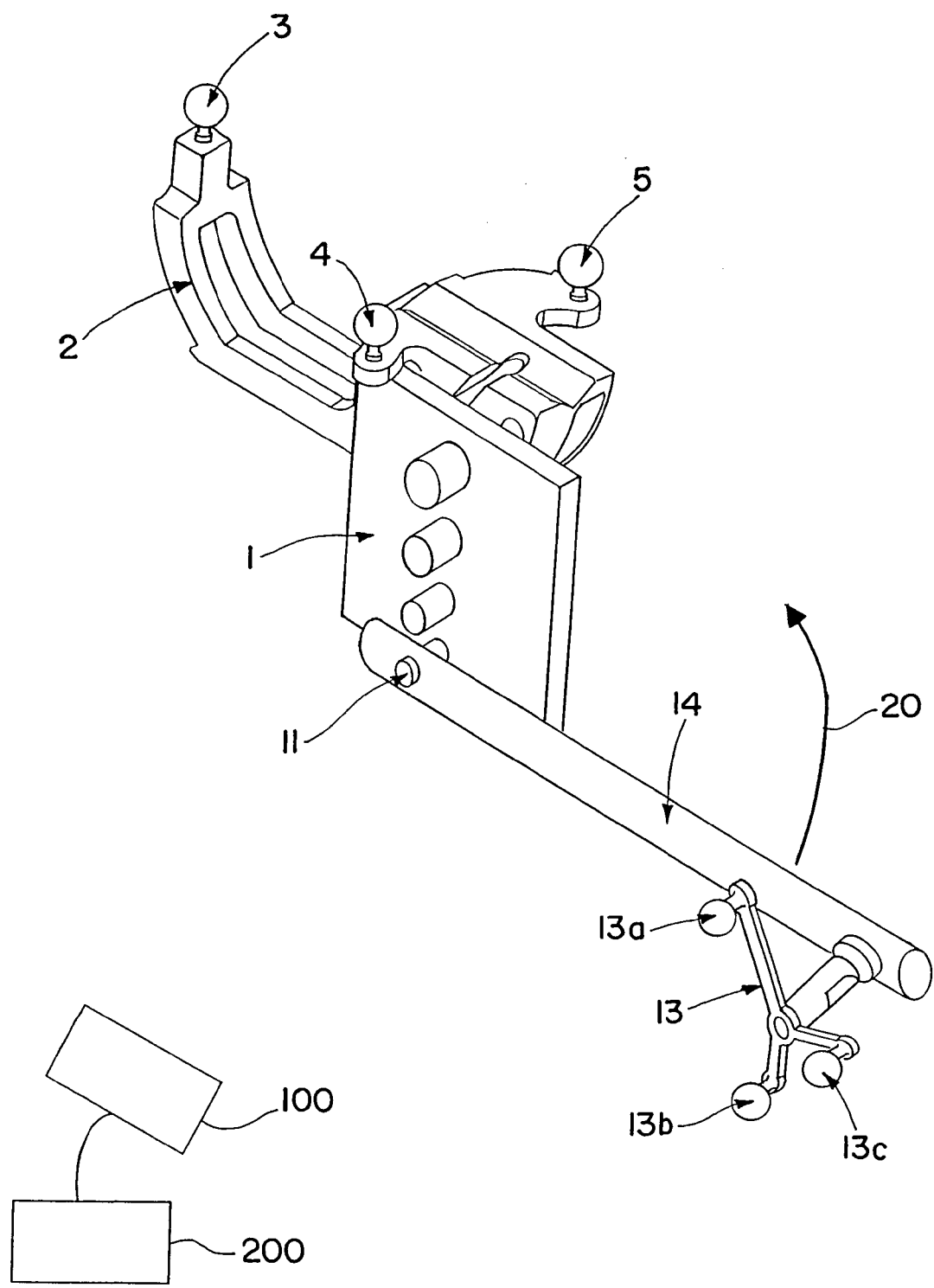
FIG. 3 illustrates an exemplary marker system in accordance with the invention.

FIG. 3 shows the assembly of a marker system in accordance with the invention. Identical reference signs duly designate identical parts, as in the preceding figures. In FIG. 3, the extension body 1 is coupled and positionally fixed to the marker unit 2 such that the extension body 1 cannot be moved relative to the marker unit 2. An exemplary instrument 14 is also shown, which can be measured in conjunction with the marker system. The rod-shaped configuration of the instrument 14 is merely by way of example. Other embodiments of the instrument, such as for example a triangular configuration, are of course possible. The extension 11 penetrates through a cylindrical opening (transit bore) in the instrument 14 in an exact fit, such that the axis of the extension 11 matches the axis of the cylindrical opening in the instrument 14. A marker means 13 is provided at an end of the instrument 14 opposite the end near which the cylindrical opening is situated. The instruments are preferably configured such that the marker means 13 is situated as far away as possible from the cylindrical opening to be measured to more exactly determine the center point of the circular trajectory 20 on which the marker means 13 is moved. The distance between the marker means 13 and the center point of the rotational movement is preferably a multiple of the diameter of the cylindrical opening, and more preferably more than five times or ten times the diameter. The present invention is applicable to instruments comprising a marker means that are suitably configured in this way.

The markers 13a, 13b and 13c can be active markers that emit signals (e.g., light or ultrasound). Preferably, however, the markers are passive markers that reflect signals emitted in their direction. An infrared light source, for example, can be provided that continuously or intermittently emits infrared light, which is reflected by the marker spheres 13a, 13b, 13c, 3, 4 and 5. The camera 100, which is preferably designed as a camera comprising two spatially separate detection elements, receives the signal (e.g., infrared light) emitted by the marker spheres 3, 4, 5, 13a, 13b and 13c. The marker spheres 3, 4 and 5 and the marker spheres 13a, 13b and 13c, respectively, are in a characteristic positional relationship with respect to each other. This characteristic positional relationship is preferably known. For example, the center points of the marker spheres 3, 4 and 5 enclose a triangle, the side lengths and angles of which are preferably known. The center points of the marker spheres 13a, 13b and 13c correspondingly enclose a triangle, the side lengths and angles of which are known. If both the marker array comprising the spheres 3, 4 and 5 and the marker array comprising the spheres 13a, 13b and 13c have thus been characterized by the side lengths and angles of the respective triangle, then the data processing means 200 can ascertain, from the data signals transmitted from the camera 100, which marker array the signals originated from.

In order to determine the position of the axis of the cylindrical opening and the diameter of the cylindrical opening in the instrument 14, the following procedure can be performed. The instrument 14 can be rotated around the axis of the extension 11 along the circular trajectory 20, such that at least three positions are detected by the camera 100 and thus also by the data processing means 200.

From the data signals emitted from the marker means 13, the data processing means 200 then calculates the center point of the circular trajectory along which the marker means 13 has moved. The center point of this circular trajectory matches the axis of the extension 11. The relative location between the marker array comprising the spheres 3, 4 and 5 and the individual extensions, in particular the extension 11, is also known. The location of the extension 11 is thus also known from the detected signals from the marker array comprising the spheres 3, 4 and 5 and from the stored relative location between the spheres 3, 4 and 5 and the respective extensions, in particular the extension 11. The data processing means can thus verify whether the center point of the circular trajectory 20 matches the location of the axis of the extension 11. If this is the case, then the location of the axis of the cylindrical opening is thus determined, since it matches the center point of the circular trajectory.

The location, for example, can be described in a reference system in which the detection means lies. Due to the known location of the center point of the circular trajectory 20 and the known location of the extension 11, it is also known that the instrument has rotated around the extension 11. Since the particular geometric properties of the extension 11, in particular the diameter of the extension 11, are stored in the data processing means, the diameter of the cylindrical opening in the instrument 14 is thus also known. Thus, both the location of the cylindrical opening and its diameter can be determined by means of the method in accordance with the invention and the marker system in accordance with the invention.

Figure 4:
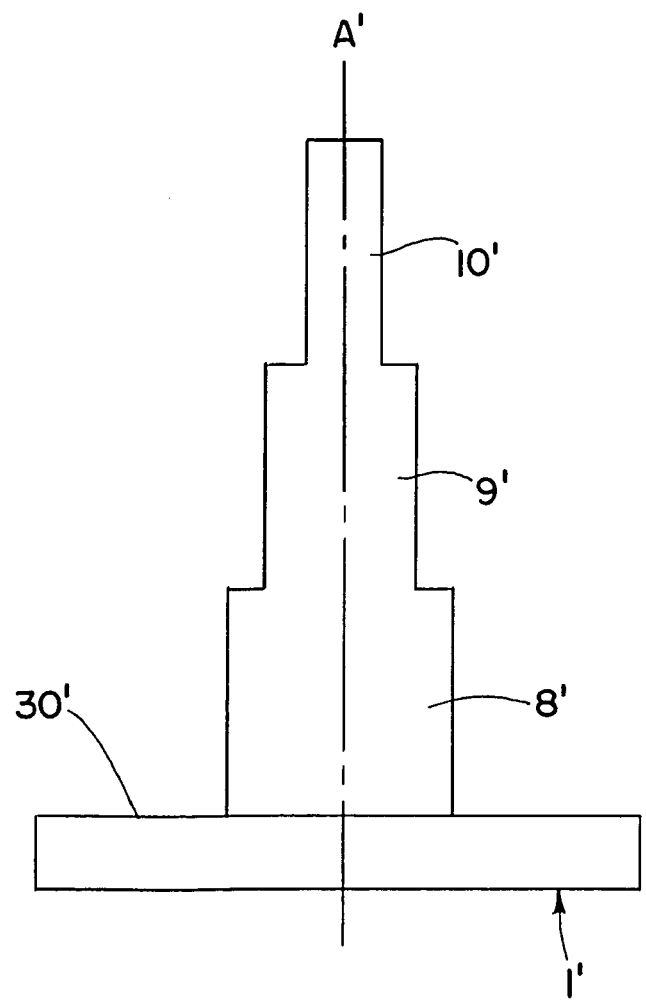
FIG. 4 illustrates an alternative arrangement of the extensions on an extension body.

FIG. 4 shows another alternative embodiment for an extension body 1'. The extension body 1' is preferably also connected to a marker means (not shown) which can for example be designed like the array 13 (reference star).

In the embodiment shown in FIG. 4, a cylindrical extension protrudes from the front face 30' of the extension body 1', wherein the diameter of said extension decreases in steps as the distance from the surface 30' increases. The height of the steps is preferably larger than the diameter of the largest extension 8'. A cylindrical opening in an instrument can also be placed onto the extension body 1' shown in FIG. 4, wherein the instrument can be moved up against one of the steps or against the front plane 30', depending on the size of the diameter of the opening. Here, too, the instrument is then preferably rotated around the respectively fitting extension 8', 9' or 10'. By detecting the signals of the marker array attached to the instrument, it is in turn possible to determine the center point of the rotational movement. It is then possible to determine from the determined location of the center point of the rotational movement which of the extensions 8', 9' or 10' the instrument has been rotated around.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A marker system for determining a shape and an axial location of a rotationally symmetrical hole in an instrument, said instrument including a plurality of instrument markers attached thereto, comprising:
    a body including a plurality of rotationally symmetrical extensions, wherein at least two extensions of the plurality of extensions are dimensionally different from one another;
    a plurality of body markers attached to said body;
    a detection device operative to detect signals emitted by said body markers and by said instrument markers and, based on said detected signals, to output data signals representative of
        a) a location of the plurality of body markers relative to the detection device and
        b) at least three different locations of the instrument markers relative to the detection device; and
    a data processing device operatively coupled to said detection device and configured to
        to receive said data signals,
        to store an association between each axis of a respective extension with at least one characteristic that defines a shape of the respective extension,
        to calculate, based on the assumption that the at least three different locations of the instrument markers lie on a circular trajectory, a location of a center point of the circular trajectory relative to the detection device, said calculation further based on the data signals corresponding to the at least three different locations of the instrument markers relative to the detection device, to determine which of the axes of the rotationally symmetrical extensions the calculated location of the center point lies on, and to determine, based on the stored association, the at least one characteristic that is associated with the determined axis.

2. The marker system according to claim 1, said data processing device configured to store relative locations between the plurality of body markers and axes of the rotationally symmetrical extensions, and wherein said determination of which axis of the rotationally symmetrical extensions the calculated location of the center point lies is based on
a) the stored relative locations between the axes and the body markers,
b) the data signals corresponding to the location of the body markers relative to the detection device, and
c) the calculated location of the center point of the circular trajectory relative to the detection device.

3. The marker system according to claim 1, wherein the instrument is a medical instrument.

4. The marker system according to claim 1, wherein a distance between adjacent extensions of the plurality of extensions is greater than a maximum diameter of any one of the plurality of extensions.

5. The marker system according to claim 1, wherein the extensions are cylindrical extensions, and the at least one characteristic is a diameter or radius of the cylinder.

6. The marker system according to claim 1, wherein the body includes a planar or convex surface, and said rotationally symmetrical extensions protrude from the planar or convex surface.

7. The marker system according to claim 1, wherein intersection points between the axes of the plurality of extensions and a surface of the body represent points that lie on a trajectory.

8. The marker system according to claim 7, wherein the trajectory is a straight, curved or closed line.

9. The marker system according to claim 1, said body comprising:
an extension body that includes the plurality of rotationally symmetrical extensions; and
a marker unit that includes the body markers,
wherein the extension body and the marker unit are releasably couplable to each other and, when coupled, maintain a spatially fixed orientation relative to each other.

10. A method for using a body to determine a shape and an axial location of a rotationally symmetrical hole in an instrument, said instrument including a plurality of instrument markers, said body including a plurality of body markers and a plurality of rotationally symmetrical extensions, wherein at least two extensions of the plurality of extensions are dimensionally different from one another, comprising:
inserting one of the plurality of extensions into the hole of the instrument, said one extension having substantially the same dimensions as the hole;
rotating the instrument around the rotationally symmetrical extension so as to define a circular trajectory;
using a detecting device to detect signals from the body markers and from the instrument markers, said detected signals representative of a location of the body markers relative to the detecting device and of the instrument markers relative to the detecting device, wherein the detected signals include signals obtained from at least three different locations of the instrument as the instrument is rotated about the inserted extension;
associating each axis with at least one characteristic that defines a shape of the respective rotationally symmetrical extension that corresponds to the respective axis;
calculating, based on the assumption that the at least three different locations lie on the circular trajectory, a location of a center point of the circular trajectory relative to the detection device;
determining the axis on which the calculated location of the center point lies; and
determining the at least one characteristic associated with the determined axis based on the stored association.

11. The method according to claim 10, further comprising storing relative locations between the body markers and the axes of the plurality of rotationally symmetrical extensions, and
wherein determining the axis in which the calculated location lies is based on the stored relative locations between the axes and the body markers, the detected signals corresponding to the location of the body markers relative to the detection device, and the calculated location of the center point of the circular trajectory relative to the detection device.

* * * * *